Figure 1:
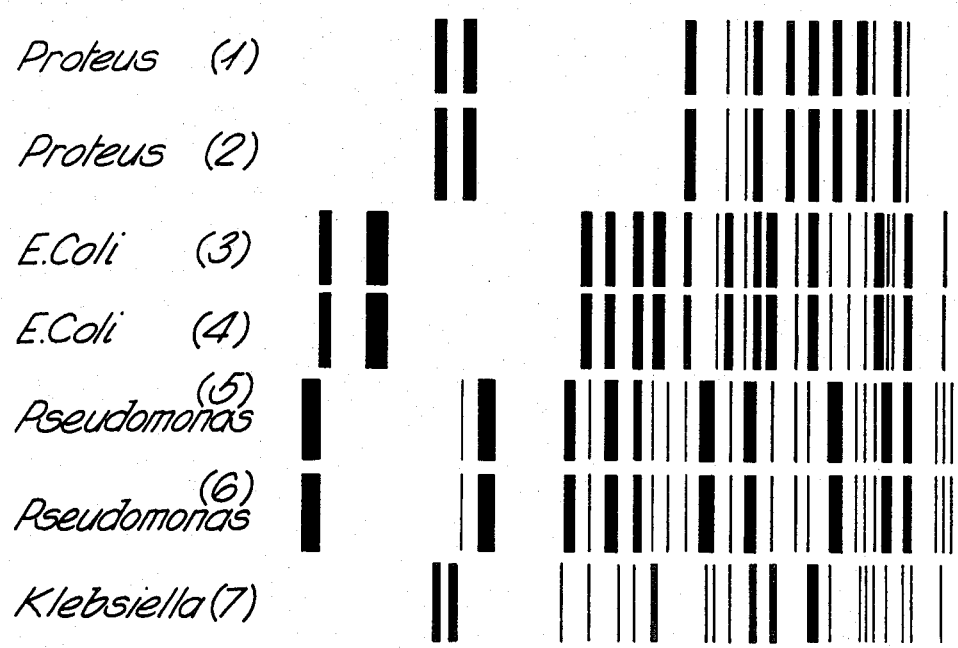

United States Patent [19]

Silman

[11] Patent Number: 4,526,865
[45] Date of Patent: Jul. 2, 1985

[54] MICROORGANISM IDENTIFICATION TECHNIQUE

[75] Inventor: Robert E. Silman, London, England

[73] Assignee: AMB Systems Corp., San Diego, Calif.

[21] Appl. No.: 341,810

[22] Filed: Jan. 22, 1982

[30] Foreign Application Priority Data

Oct. 1, 1981 [GB] United Kingdom ............... 8129683

[51] Int. Cl.$^3$ ................. C12Q 1/16; C12Q 1/04; C12Q 1/10; G01N 33/58
[52] U.S. Cl. ......................................... 435/35; 435/38; 435/34; 435/808; 435/803; 436/63; 436/56
[58] Field of Search ............. 435/29, 34, 35, 38, 435/814, 820, 808, 803; 23/230 B; 424/1, 1.5; 436/56, 63; 204/403

[56] References Cited

U.S. PATENT DOCUMENTS

| 2,914,447 | 11/1959 | Levin | 435/35 |
| 3,470,373 | 9/1969 | Brewer et al. | 435/808 |
| 3,673,410 | 6/1972 | Waite et al. | 435/35 |
| 3,858,045 | 12/1974 | Waters | 435/35 |
| 3,935,073 | 1/1976 | Waters | 435/35 |
| 3,944,471 | 3/1976 | Waters | 435/35 |
| 3,969,496 | 7/1976 | Schrot | 435/35 |
| 3,997,404 | 12/1976 | Waters | 435/35 |
| 4,057,470 | 11/1977 | Schrot | 435/35 |
| 4,142,939 | 3/1979 | Morse et al. | 435/29 |
| 4,288,543 | 9/1981 | Sielaff et al. | 435/34 |

FOREIGN PATENT DOCUMENTS 649751 4/1979 U.S.S.R. ................................ 435/35

OTHER PUBLICATIONS

Tsukamura et al., "Thin Layer Chromatography after Incubation with 35 S–Methionine, Meaning of Petroleum Ether Soluble Frac." Kekkaku 55(12) (1980), pp. 525–530, Chemical Abstracts 94: 135993n.
El-Sharkawy et al., "Differentiation Among Xanthamonas Species by Polyacrylamide Gel Electrophoresis of Soluble Protein" Journal of General Microbiology 68 (1971), pp. 155–165.
Theodore et al., "Polyacrylamide Gell Electrophoresis of Bacterial L–Forms and Mycoplasma Species of Human Origin" Applied Microbiology 21(2) (2–1971), pp. 272–277.
Lotan et al., "Plasma Membranes of Eukaryotes" in Advanced Cell Biology by Schwartz et al., Van Nostrand Reinhold Co., NY (1981), pp. 129–133.
Larsen et al., "Polyacrylamide Gel Electrophoresis of Corynebacterium Diptheriae: A Possible Epidemiological Aid" Applied Microbiology 22(5) (1971), pp. 885–890.
Razin et al., "Identification of Mycoplasma and Other Microorganisms by Polyacrylamide-Gel Electrophoresis of Cell Proteins" Journal of Bacteriology 94(6) (1967), pp. 1807–1810.
Winkelman et al., "Automatic Calculation of Desitometer Scans of Electrophoretic Strips" Clinical Chemistry 15(8) 1969, pp. 708–711.
Robinson, "Starch Gel Electrophoresis of Bacterial Cell Free Extracts" Lab. Pract., 17(2), pp. 196–198, Chemical Abstracts 68: 66260v.
Flygare et al., "Electrophoretic Light Scattering" Electro-Opt., Ser. 1 (part 1) (1976), pp. 321–366.
Lawson, "Medical and Environmental Applications of Quadrupole Mass Spectrometry" Quadrupole Mass Spec., (1976), pp. 307–333, C.A. 86: 52267n.

*Primary Examiner*—Robert J. Warden
*Assistant Examiner*—J. E. Tarcza
*Attorney, Agent, or Firm*—Michael Ebert

[57] ABSTRACT

An identification technique for micro-organisms in which a dilute solution of a culture medium containing an unknown micro-organism has added thereto an emissive agent such as a radioactive amino acid to produce a mix of emissive products that depends on the metabolic mechanism of the micro-organism. After a predetermined incubation period, the reaction is arrested and the solution layered onto a gel plate where it is subjected to electrophoresis. The plate is then autoradiographed by exposing the gel to a sensitive photographic film for a period sufficient to produce thereon a characteristic band pattern functioning as an identifier for the micro-organism. Identification may be effected by comparing the identifier for the unknown with a collection of identifiers for known micro-organisms to find a match with one of these known identifiers. The comparison is preferably carried out by scanning the unknown identifier to produce a signal which is compared with signals representing known identifiers stored in a computer which, when a match is found, yields identification data. Alternatively, the emissive products, after separation, may be detected by direct scanning to provide an identifier signal for computer processing.

16 Claims, 3 Drawing Figures

MICROORGANISM IDENTIFICATION TECHNIQUE

BACKGROUND OF INVENTION

This invention relates generally to the identification of micro-organisms, and more particularly to a technique whereby a bacterium or virus may be identified by the characteristic band pattern of radioactive particles it generates under standardized conditions, the identified organism being quantified by the intensity of the pattern.

Identity is generally defined as "sameness in all that constitutes the objective reality of a thing". Though the concern of the invention is with the identification of micro-organisms, the problem of how best to carry out identification arises in those situations in which one must determine whether an unknown object, in all essential respects, matches a particular known object lying within a large collection of diverse known objects. In the context of microbiology, the term identification, as used herein, encompasses the determination of whether an unknown microbe falls within a particular class or genus of microbes as well as determining whether the microbe is of a particular type, species or strain.

The logical approach to the problem of identification is to find or create an identifier in the form of a symbol, signature, fingerprint or other indicia functioning to specify a particular object and no other in the collection. Thus while billions of individuals exist who differ from each other in sex, age, height, weight, shape, eye colour and in many other respects, a unique identifier is the individual's fingerprint. Hence if one has a collection or library of fingerprints covering all persons having a criminal record, by taking a fingerprint of an individual whose record is unknown, one can, by consulting the library, determine whether that fingerprint matches a particular print in the library.

Lacking an individual's fingerprint or identifier, identification would require matching of a large number of variables, such as sex, height, weight, etc., a relatively complicated procedure with uncertain results should only limited information be available as to the many variables involved. As will later be explained, it is the absence of an identifier for micro-organisms which presently complicates identification procedures in microbiology.

But the existence or creation of an identifier is only a partial solution to the problem of identification. An identifier is of limited practical value if it is not "machine readable" and therefore requires visual comparison to ascertain whether the identifier for an unknown unit matches a particular identifier in a library of known units.

Thus in the case of fingerprints, for many years the process of determining whether a match existed between a given fingerprint and one in a collection of known prints involved visual inspection carried out by fingerprint experts. However, use is currently made for this purpose of electro-optical scanners operating in conjunction with computers to automate fingerprint matching procedures.

Similarly, in the case of the large collection of diverse grocery and other items sold in supermarkets, in order to expedite the handling of these products at checkout counters and to facilitate inventory control and accounting procedures, use is now made of identifiers based on the Universal Product Code (UPC) whereby each product has printed thereon a UPC symbol. This symbol is in the form of a machine-readable bar code having digits identifying the manufacture of the product and digits identifying the product itself, so that each product has a unique bar code.

By electro-optically scanning the symbol on each purchased product and generating a corresponding signal, one is able in an associated computer whose memory has digitally stored therein the full range of supermarket products, to compare the signal derived from the scanned symbol with the stored information and to extract from the computer, when a match is found, the identity of the purchased product and its price.

Thus in the above-described situations, computer technology is exploited to facilitate identification procedures, use being made of machine-readable identifiers. But in the realm of microbiology in which identification plays a vital role, the identification procedures presently practised do not make use of identifiers for micro-organisms. Existing procedures require skilled laboratory personnel and are tedious and time-consuming; for when a specimen of an unknown micro-organism is developed, it must be visually examined under a microscope and then compared with available data regarding known forms.

These procedures represent a significant cost factor in microbiological studies, and by their very nature are subject to visual fatigue and human error. In recent years, the need for efficient and relatively rapid identification techniques has become more pressing because of the remarkable expansion of environmental and industrial microbiology, and genetic engineering. An interesting use of selected micro-organisms to degrade products of industrial organic syntheses is described in GB-PS 2,010,327A.

Techniques are available to determine the morphology of individual biological cells. Also well developed are procedures for growing or cultivating micro-organisms in the laboratory on nutrient material, some of these procedures requiring special conditions such as the absence of free oxygen. By incubating a nutrient agar-type medium, using the streak-plate or pour-plate method, cells are individually separated. In incubation, individual cells reproduce rapidly to generate a visible colony of cells, each colony being a pure sample of a single kind of micro-organism. In order to identify an unknown cell, existing techniques call for the use of high-magnification optical or electron microscopes. These procedures for the identification of bacteria are set forth in detail in chapter 5 of the text "Clinical Bacteriology"—Fifth Ed.—J. Stokes et al., published by Arnold (London) 1980.

Modern diagnostic medical practice is divided into specialized areas. Thus physicians who treat venereal disease must investigate and identify a class of micro-organisms that may differ from the class of concern to doctors specializing in blood or other disorders. To assist their doctors, hospitals make use of medical service laboratories which receive urine, blood and other specimens and are required to analyse and identify pathological organisms. Present service laboratory procedures for this purpose employ the traditional techniques of plating, staining and microscopy supplemented by a battery of individual tests for different types of micro-organism. These procedures entail a high order of technical skill and are labour-intensive. While most laboratory technicians are highly competent, the fact remains that mistaken identifications of pathological organisms are not uncommon in a period in which service laboratories operate under heavy work loads. And though in recent years automated procedures are now carried out in service laboratories for other purposes, the identification of micro-organisms has not heretofore enjoyed the benefits of automation.

Inasmuch as the present invention provides a technique for facilitating the identification of micro-organisms by creating for each organism a machine-readable identifier which is indirectly derived from the genetic code implanted therein, we shall now briefly review the fundamental nature of micro-organisms.

The cell is the basic unit of life both in terms of structure and function. A bacterium is a single-celled microorganism in which the cell not only is the structural unit but the entire organism. In contradistinction, in multicellular organisms, the cells are combined into units which are integrated into a system which constitutes the living organism. A virus, on the other hand, is a parasite; for it is obligated to grow within an appropriate host cell and cannot multiply outside this cell. When a virus enters a living cell, it is capable of creating hundreds of identical particles, the virus exploiting the host cell's energy and biological mechanism for this purpose.

A typical cell is enclosed by a membrane within which is contained a nucleus, the differentiated nucleoprotein-rich protoplasm of the cell. The living matter between the cell membrane and the nucleus is the cytoplasm which incorporates various structural or particulate entities. The term "bacterium" is applicable to any of a group of diverse procaryolic single-celled oganisms; that is, a cell having no internal membranes which separate the nucleus from the cytoplasm.

The nuclear material or DNA (deoxyribonucleic acid), the chemical substance responsible for the transmission of heréditary data, occupies a position near the centre of a bacterial cell. This material is the entire genetic apparatus of the bacterium and consists of a single, circular chromosome to which all genes are linked, each gene being a repository of a unit of genetic information. DNA is a long, ropelike molecule consisting of two strands, each wound about the other to form a double helix.

Also present in the cell is another type of nucleic acid, RNA (ribonucleic acid). RNA, which is composed of a single strand, acts to process the information coded in DNA for protein synthesis. Such synthesis is effected by ribosomes, which are large RNA protein particles in the cytoplasm of the bacterial cell. Before protein synthesis can take place, the code borne by DNA must first be exported to a substance that conveys information from the DNA in the nuclear region to the ribosomes in the cytoplasm. This substance is known as messenger RNA or mRNA.

The process by which a complementary single-stranded mRNA is synthesized from one of the DNA strands is referred to as "transcription". Transcription is the first step in gene expression. The next step is translation, the process by which the genetic information now locked in the mRNA molecule governs protein synthesis.

The genetic information or genotype of a cell is determined by data contained in its chromosome which is divided into genes. A gene consists of hundreds of nucleotide pairs and it specifies the formation of a particular polypeptide; e.g., a chain formed by a plurality of amino acids linked by peptide bonds. Thus if a polypeptide chain is constituted by 200 amino acids, then the gene coding for this polypeptide must contain 600 base pairs, three bases for each amino acid. A bacterial chromosome has the capacity to code for about 3000 different proteins, a protein being composed of an extremely large number of amino acids joined by peptide bonds.

In short, the deciphering of the genetic code carried by the DNA and its application to the production of proteins essential for all growth and activity, entail "transcription" to transfer information from DNA to RNA, and "translation" to convert RNA information into protein.

In microbiology, micro-organisms are classified in taxonomic categories, nomenclature being used to name the units delineated and characterized by classification. Identification involves the use of criteria established for classification and nomenclature in order to identify micro-organisms by comparing the characteristics of an unknown unit with known units. Thus with a newly isolated micro-organism, its identification requires an adequate characterization thereof and then a comparison with published descriptions of other similar micro-organisms.

For the reasons set forth above, because existing microbiological identification procedures do not make use of identifiers in the form of a symbol or other indicia, these procedures are time-consuming, labour-intensive and expensive.

With a view to automating the identification of pathological organisms, U.S. Pat. No. 4,288,543 to Sielaff et al discloses a procedure in which the susceptibility of various strains of bacteria to antimicrobial agents is tested, this being done in conjunction with a determination of the light-scattering index of the bacteria being tested. The numerical growth data obtained by the light scatter comparisons are analysed by computer-assisted techniques to identify the strains of bacteria.

The admitted drawback to this patented procedure is that one must use agents not in common therapeutic use in order to avoid errors resulting from strains which have become immune to various therapeutically utilised antibiotic agents. The Sielaff patent also makes of record other patents and publications dealing with the automated, rapid identification of bacteria by computer analysis of growth inhibition patterns. Though these computer-assisted procedures represent, at least in theory, a significant advance over classic procedures for the identification of microbes, the basic problem of identification is not obviated thereby, for the microbes are not supplied with unique markers or identifiers to facilitate their positive identification.

SUMMARY OF INVENTION

In view of the foregoing, the main object of this invention is to provide an identification technique for micro-organisms in which a micro-organism to be identified has added thereto an emissive agent such as a radioactive aminoacid to produce an emissive specimen whereby a radiograph of the specimen takes the form of a characteristic band pattern that may be compared with patterns in a library of band patterns derived from known micro-organisms to positively fix the identity of the unknown organism. Alternatively, the emissive specimens may be directly scanned to generate signals which are then processed in a computer to perform identification procedures.

A significant advantage of the invention is that by creating a unique tag or identifier for each micro-organism, identification thereof is carried out without the need for magnification and visual examination of the organism itself, thereby dispensing with tedious and time-consuming inspection procedures and the uncertainties incident thereto.

More particularly, an object of the invention is to provide a technique for producing radioactive specimens of micro-organisms in a form creating a radiographic band pattern which is machine-readable, whereby the patterns may be electro-optically converted into signals that can be digitized and stored in a digital computer to create a library of identifiers for known micro-organisms, thereby facilitating the automatic comparison of an unknown micro-organism with those in the library to find a match themselves.

Briefly stated, these objects are attained by an identification technique for micro-organisms in which a diluted solution of a culture medium containing the micro-organism to be identified has added thereto an emissive agent such as a radioactive amino acid to produce a "mix" of emissive products that depends on the metabolic mechanism of the microbe. Herein, the expression "metabolic mechanism" is to be broadly construed and includes genetic mechanisms. While each item or protein product in a given mix may be found in mixes derived from other organisms, the factor which renders the mix unique to a particular organism is the relative proportions of the items in the mix, for these proportions characterise no other organism and are therefore singular. After a predetermined incubation period, the reaction is arrested and the solution is layered onto a gel plate where it is subjected to electrophoresis. The plate is then autoradiographed by exposing the gel to a sensitive photographic film for a period sufficient to produce therein a characteristic band pattern functioning as an identifier for the micro-organism.

Identification may be effected by comparing the identifier for the unknown micro-organism with those stored in a collection of identifiers for known micro-organisms to find a match with one of the known identifiers. This comparison is preferably carried out by electro-optically scanning the unknown identifier to produce a signal which is compared with signals representing known identifiers stored in a computer; the computer, when a match is found, yields identification data. Alternatively, the emissive products, after separation, may be detected by direct scanning to provide an identifier for computer processing.

OUTLINE OF THE DRAWINGS

Figure 2:
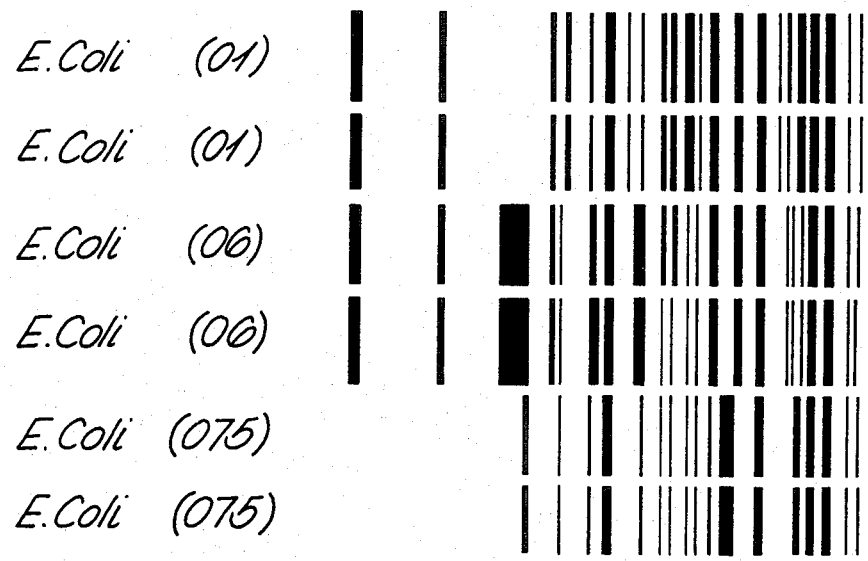
Figure 3:
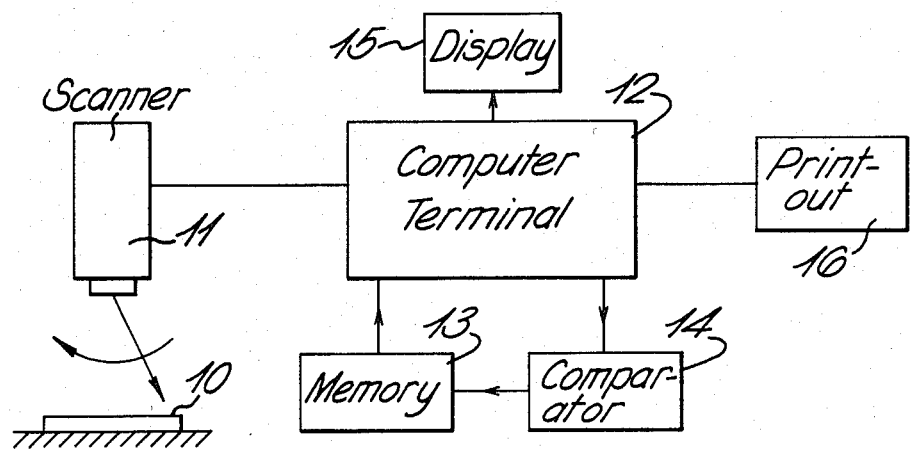

For a better understanding of the invention, as well as other objects and further features thereof, reference is made to the following detailed description to be read in conjunction with the accompanying drawings, wherein:

FIG. 1 gives examples of band patterns derived from different types of bacteria in a technique in accordance with the invention;

FIG. 2 gives examples of band patterns derived from different strains of a single type of bacteria; and FIG. 3 is a simplified block diagram of a computerised system for automatically carrying out an identification procedure in accordance with the invention.

DESCRIPTION OF INVENTION

The present invention is based on a discovery unexpectedly made in the course of research in which the function of messenger RNA in particular tissues was being investigated. In this investigation, messenger RNA was extracted from tissue and purified. Then the messenger RNA was translated into corresponding peptide/protein by adding thereto a cell-free system constituted by a ribosomal mixture with little or no genetic information of its own, but having the capacity to translate exogenous messenger RNA. As a consequence, the free amino acids in the translation medium were incorporated into the peptide/protein in a sequence dictated by the messenger RNA derived from the tissue.

In order to identify the products of the translation system, a radioactive amino acid ($S^{35}$ methionine) was added to the system. Methionine is a sulphur-containing amino acid important to biological trans-methylation processes. $S^{35}$ is radioactive sulphur of mass number 35 that can be derived by pile radiation of elemental sulphur.

After a translation period lasting about two hours, the translation medium was layered onto a gel plate and subjected to electrophoresis. Electrophoresis is the migration of colloidal particles in a liquid due to a potential difference established across immersed electrodes, the migration being toward the electrode of a charge opposed to that of the particles. Electrophoresis is applicable to proteins, for its molecules act as colloidal particles, and their charge is negative or positive, depending on whether the surrounding solution is acidic or basic.

All free amino acids ran through the system, while all amino acids which had been incorporated into newly translated particles were adsorbed on the plate at chromatographic positions characteristic of the peptide into which they had been incorporated. Similarly, any $S^{35}$ methionine which had been incorporated into a peptide would be contained within it and thereby function as a marker for the molecules.

The gel plate was then placed against a sensitive photographic plate. Appearing on the negative as a result of radioactive emission from the $S^{35}$ methionine, were bands occupying positions thereon appropriate to the molecule in which the radioactive amino acid had been incorporated.

In this negative, the bands had an intensity proportional to the amount of $S^{35}$ methionine incorporated into the peptide, i.e., to the number of methionine amino acids in the peptide and to the quantity of peptide that had been synthesized.

One would expect, when following this procedure, that in the absence of a message, no bands except for endogenous background translation would appear on the photographic negative. But contrary to this expectation, bands were developed which did not seem to correspond in any way to the messenger RNA that had been added to the translation system. Moreover, it was found that bands were created even when no RNA from any source whatever had been added to the system.

The conclusion then reached was that the unexpected appearance of bands could only be imputed to bacterial contamination, and that it was bacterial RNA that was being translated. This conclusion was confirmed when the bands were caused to disappear by sterilizing the various solutions that were being used in this research programme.

It was also observed that different solutions gave rise to different band patterns, each solution producing a unique pattern quite distinct from those emanating from the other solutions. It was discovered that these distinctive band patterns occurred because the solution from which they were derived were contaminated with different types of bacteria, each generating a different pattern of translated peptides. This lead to the principle underlying the present invention—namely, that bacteria, viruses, fungi and other micro-organisms can be identified and typed by the pattern of radioactive peptides produced under standard conditions, and that the identified micro-organism can be quantified by the intensity of the characteristic radioactive peptides.

The present practice in identifying bacteria is to plate the micro-organism onto agar gels, the growth of the bacteria producing characteristic colonies on the plate. Identification is further facilitated by staining. The bacteria are then visually examined under a microscope. Substrains can be identified by serotyping where the particular bacterial strain is added to antibody raised against that strain and the titre of the reaction noted.

In an identification technique in accordance with the invention, a dilute solution of a culture medium containing the micro-organism to be identified has added thereto a radioactive amino acid. After a predetermined incubation period, the reaction is arrested and the solution then layered onto a gel plate where it is subjected to electrophoresis. The plate is then autoradiographed by exposing the gel to an X-ray film for a period sufficient to produce a characteristic band pattern. The band pattern serves as an identifier for the unknown micro-organism and its identity is established by comparing it with band patterns derived from known forms of micro-organism.

It is important to understand that the band pattern derived from a particular organism depends on the conditions under which the specimen is produced, such as the nature of the radioactive amino acid, the degree of dilution, the period of incubation and all other variables involved. Hence it is desirable in order to provide a constant identifier unique to each micro-organism, that these conditions be standardised. To facilitate standardisation a reference standard may be established in a form which can be fed as reference data into a computer. Subsequent samples may thereafter be checked by the computer with the reference to see whether a search lies within an acceptable tolerance band. Under standardised conditions, the band pattern from a given micro-organism is always substantially the same. The micro-organism in question may be quantified by the intensity of the characteristic band pattern produced under the standardised conditions.

The band pattern derived from each organism constitutes a bar code which is an indirect function of the genetic code implanted in the organism. But it does not reflect this genetic code; for the form of the band bar code is affected by the conditions under which it is produced and has a repeatable form for a given organism only if these conditions are standardised. And because it is a bar code, it may be scanned and analysed by techniques presently in use for bar codes in computer technology.

EXAMPLE I

To identify different types of bacteria, a 1/100 dilution was made of culture mediums containing Proteus, E. coli, Pseudomonas and Klebsiella, each cultured in duplicate.

Five microliters of solution was taken from each sample, to which was added five microliters of $S^{35}$ methionine. No translation system was added. After a two-hour incubation period, the reaction was arrested by adding 10% SDS (sodium dodecyl sulfate) and 3% mercaptoethanol in trisbuffer. Each solution was then layered onto a polyacrylamide gel plate.

After carrying out electrophoresis for sixteen hours at 35 volts, the gel was fixed for three hours, dehydrated with acetic acid washes and exposed to a 2,5-diphenyloxazole/acetic acid mixture for three hours. The plate was then water-washed and dried to provide the desired specimen. Finally the plate was autoradiographed by exposing the gel to an X-ray film overnight.

A trace of the resultant autoradiographed is shown in FIG. 1 wherein channels 1 and 2 are the duplicates of Proteus; channels 3 and 4, the duplicates of E. coli; channels 5 and 6, the duplicates of Pseudomonas; and channel 7, Klebsiella.

It will be evident from an examination of FIG. 1 that the pattern of bands in channels 1 and 2 are identical so that duplicate samples of Proteus give rise to the same bar code identifier. This is also true of E. coli in channels 3 and 4 or Pseudomonas in channels 5 and 6; and Klebsiella in channel 7 is different from the other bar codes.

EXAMPLE II

The above-described procedure was repeated for a second five microliters from each of the cultures. The resultant autoradiograph was indistinguishable from that shown in FIG. 1, thereby indicating that under standardised conditions, each bacterium gave rise to a distinctive band pattern readily distinguishable from those produced by the other bacteria. It is therefore possible with the naked eye to identify each bacterium by means of its autoradiographed identifier.

EXAMPLE III

To determine whether it was possible to identify different strains within a single bacterial type, three different strains of E. coli were cultured in duplicate (01-06-075) and treated in the same manner described above to produce an autoradiograph.

As shown in FIG. 2, the band patterns for the duplicate 01 strain are the same, this being true of the band patterns for the duplicate 06 and 075 strains. But there are significant differences in the band patterns for the different strains which serve to distinguish the identifiers from each other. However, the differences in this case are not as pronounced as when different types of bacteria are involved.

EXAMPLE IV

To identify anaerobic bacteria and their strains, the following procedure was followed: Bacillus vulgates and three strains of B. fragilis and B. thetaiota were treated in the same manner described above in the first example, except that the two hour incubation period was performed under anaerobic conditions, and five microliters of neat culture medium was used rather than a 1/100 dilution. The resultant autoradiograph revealed band patterns that were distinctive for each of the specimens tested, so that the band patterns functioned as bar code identifiers thereof, making it possible with the naked eye to distinguish different types of anaerobic bacteria and different strains within the types.

Automated Procedures:

Referring now to FIG. 3, there is shown a computerised system for scanning a band pattern formed on a radiographic plate 10, the pattern or bar code being an identifier for an unknown micro-organism.

This pattern is electro-optically scanned by a scanner 11, such as a scanner of the type used in UPC supermarket systems, as disclosed in the U.S. Pat. to Kaslow No. 3,959,624.

The output of scanner 11 is a video signal whose wave form reflects the scanner pattern. This signal is converted into a digitised signal for processing in a computer terminal 11. Computer terminal 12 operates in conjunction with a memory 13 in which is stored a library of signals, each representing the unique band pattern of a known form of micro-organism.

The function of the computer system is to identify the unknown micro-organism whose band pattern has been scanned. To this end an electronic comparator 14 is provided which acts to sequentially compare the input signal from the scanned pattern of the unknown micro-organism with the signals in memory 13 to find a match between the input signal and one of the stored signals representing various known forms of micro-organisms. When a match is found, information regarding the selected stored signal is conveyed to computer terminal 12 whose output then provides on a visual display 15 a read-out of the known micro-organisms, and on an associated print-out 16, a hard copy of the reading.

In practice, the computer may store not only the names of known micro-organisms, but also data in regard to the nature and characteristics thereof. These stored data can be printed out, so that the user of the system is informed not only as to the identity of the unknown micro-organism, but also useful information relevant thereto.

Another approach obviating the need for visual inspection of the band pattern in determining the identity of an unknown micro-organism is to electro-optically scan the pattern to produce a signal which is converted into a multi-digit code number unique to the pattern. A scanning system capable of converting a pattern into a unique code number is disclosed in the U.S. Pat. No. 3,581,282 to Altman wherein the pattern is that produced by the palm of the hand, the Altman system serving to identify individuals.

By converting band patterns into code numbers in the manner taught by Altman, one can then create a directory of code numbers and in which each code number is related to a known type or strain of micro-organisms. Thus one who wishes to identify an unknown micro-organism, first produces a radiograph in the manner disclosed hereinabove, and then by means of a scanning system of the Altman type, converts the band pattern into a code number. Once he has the code number, it becomes a simple matter to consult the code directory to fix the identity of the unknown micro-organism.

General Principles and Alternative Procedures Based Thereon

The procedure described in the foregoing sections of the specification represents but one possible technique base on the general principle underlying the invention. Under this principle, any emissive substrate can be used, provided that it is incorporated into products of metabolism and catabolism which uniquely identify the micro-organism. The methodology is therefore not limited to radioactive amino acids, such as $S^{35}$ methoinine or $H^3$ leucine, and protein. In practice use may be made of emissive nucleic acids, long chain fatty acids, carbohydrates and membrane units to produce a "mix" of emissive products. As long as this mix is the result of the specific metabolism of the micro-organism and can thereby be used to identify the micro-organism, it does not matter where or how the metabolic mechanism of the microbe is being harnessed.

The mix of emissive products lends itself to identification only if the products are separated from each other in a manner displaying the unique characteristics thereof. Electrophoresis, as described above, is a highly discriminating method for segragating proteins. Another acceptable method for protein separation is isoelectric focusing in which proteins are caused to separate across a plate and to fix themselves at their isoelectric points. Affinity, molecular sieve, ion exchange and thin layer chromatography may also be used for separation.

Once the mix is separated, then the separated emissive products can readily be detected to fix the identity of the microbe. The invention is not limited to detection by means of radiographic techniques, for emissions may be sensed by other known means. For example, use may be made of a direct scanner or a video camera in which the emissions are caused to impinge on a plate sensitive thereto, the plate being scanned by an electron beam to generate a video signal. The video signal may then be digitised and processed in a computer to effect identification.

As pointed out previously, for purposes of identification it may not always be necessary to find the exact identity of the microbe, and to determine for example that the microbe is E. coli or Pseudomonas. In some situations, it may be sufficient for purposes of identification to determine whether the unknown is a bacterium, a fungus or a virus, that is whether the microbe falls within a given known class. To this end the computer is governed by an algorithm or programme operating in conjunction with an appropriate data bank so as to process the output of the specimen scanner or detector to identify the unknown with respect only to class.

Thus, the process of identification in the context of the present invention, lies in determining whether an unknown microbe lies within or matches a class, a species, a strain or any other established or predetermined frame of reference. In that sense, a system in accordance with the invention has a degree of resolution that depends on the task assigned thereto.

To overcome difficulties in maintaining absolutely standard conditions for determinations, the detection system may be calibrated, for example by detecting the emission products of a known control, which emission products have been obtained and separated under the same conditions as the emission products of the unknown. The signal of the unknown is then modified (to a degree determined by the difference between the control signal and a corresponding signal stored in the data bank) in order to obtain a proper comparison of the unknown with the stored data.

While there have been shown and described preferred embodiments of a micro-organism identification technique, it will be appreciated that many changes and modifications may be made therein without, however, departing from the essential spirit thereof.

I claim:

1. A technique for identifying an unknown micro-organism comprising the steps of:
   A. Preparing a specimen of the micro-organism to which a radioactive emissive agent has been added that is actively incorporated into the products of metabolism of the micro-organism to produce a mix of radioactive peptide or protein emissive products in a manner that depends on the metabolic mechanism of the micro-organism, B. separating the peptide or protein emissive products in the mix resulting from said preparation of a specimen, C. detecting the separated peptide or protein emissive products to derive a characteristic pattern therefrom that depends on the conditions under which the specimen is prepared, which conditions are standardized to provide a repeatable characteristic pattern functioning as a unique identifier for the unknown micro-organism, and D. comparing the identifier for the unknown micro-organism with stored information relating to the characteristic patterns of known micro-organisms to determine the identification of the unknown.

2. A technique as set forth in claim 1, wherein said emissive agent is a radioactive amino acid.

3. A technique as set forth in claim 2, wherein said separation is effected by electrophoresis.

4. A technique as set forth in claim 3, wherein said detection is effected by radiography.

5. A technique as set forth in claim 1, wherein said preparation is carried out by:

A. forming a solution of a culture containing the micro-organism:

B. adding to the solution a radioactive amino acid:

C. incubating the solution for a predetermined period:

D. layering the incubated solution onto a gel plate and then subjecting the solution to electrophoresis to provide said specimen.

6. A technique as set forth in claim 5, wherein said radioactive amino acid is $S^{35}$ methionine.

7. A technique as set forth in claim 5, wherein said micro-organism is a bacterium.

8. A technique as set forth in claim 5, wherein the incubation step is carried out for a period of about 2 hours.

9. A technique as set forth in claim 8, wherein the incubation reaction is arrested after the incubation period.

10. A technique as set forth in claim 5, wherein said gel plate is a polyacrylamide gel plate.

11. A technique as set forth in claim 5, wherein said specimen is autoradiographed on X-ray film to produce a bar code pattern.

12. A technique as set forth in claim 11, wherein said film is exposed for at least 6 hours.

13. A technique as set forth in claim 1, wherein said comparison is between the identifier for the unknown and a collection of identifiers representing various known micro-organisms to find a match with one thereof, thereby identifying the unknown.

14. A technique as set forth in claim 13, wherein said comparison is effected by electro-optically scanning said unknown identifier to produce an input signal representative thereof, and comparing said input signal in a computer with signals stored therein which represents a collection of known micro-oganisms.

15. A technique as set forth in claim 13 wherein said comparison is effected by electro-optically scanning said unknown identifier to produce a signal representative thereof and converting said signal into a code number which is compared with a collection of code numbers representing various known micro-organisms.

16. A technique for identifying an unknown micro-organism comprising the steps of:

A. preparing a specimen of a culture of the micro-organism to which a radioactive emissive agent in the form of a free amino acid has been added that is actively incorporated into the products of metabolism of the micro-organism to produce a mix of radioactive peptide or protein emissive products in a manner that depends on the metabolic mechanism of the microorganism, B. separating the emissive products in the mix resulting from said preparation of a specimen, C. detecting the separated emissive products to derive a characteristic pattern therefrom that depends on the conditions under which the specimen is prepared, which conditions are standardized to provide a repeatable characteristic pattern functioning as a unique identifier for the unknown micro-organism, and D. comparing the identifier for the unknown micro-organism with stored information relating to the characteristic patterns of known micro-organism to determine the identification of the unknown.

* * * * *